(12) United States Patent
Jeong et al.

(10) Patent No.: US 8,716,304 B2
(45) Date of Patent: May 6, 2014

(54) PREPARATION METHOD OF MLN4924 AS AN E1 ACTIVATING INHIBITOR

(75) Inventors: Lak Shin Jeong, Seoul (KR); Hyuk Woo Lee, Gyeonggi-do (KR)

(73) Assignee: EWHA University—Industry Collaboration Foundation, Seoul (KR)

( * ) Notice: Subject to any disclaimer, the term of this patent is extended or adjusted under 35 U.S.C. 154(b) by 78 days.

(21) Appl. No.: 13/425,212

(22) Filed: Mar. 20, 2012

(65) Prior Publication Data

US 2012/0330013 A1 Dec. 27, 2012

(51) Int. Cl.
*A01N 43/90* (2006.01)
*A61K 31/519* (2006.01)
*C07D 497/00* (2006.01)

(52) U.S. Cl.
USPC ........................................ 514/265.1; 544/280

(58) Field of Classification Search
None
See application file for complete search history.

(56) References Cited

U.S. PATENT DOCUMENTS

2007/0191293 A1   8/2007  Langston et al.

OTHER PUBLICATIONS

Lee, et. al., Journal of Organic Chemistry (2011), 76(9), 3557-3561.*
Haas, A. L. et al., "The Mechanism of Ubiquitin Activating Enzyme", *J. Biol. Chem.* 257(17):10329-10337, Sep. 10, 1982.
Bohnsack, R. N. et al., "Conservation in the Mechanism of Nedd8 Activation by the Human AppBp1-Uba3 Heterodimer", *J. Biol. Chem.* 278(29):26823-26830, Jul. 18, 2003.
Soucy, T. A. et al., "An inhibitor of NEDD8-activating enzyme as a new approach to treat cancer", *Nature* 458:732-737, Apr. 9, 2009.
Lee, H. W. et al., "Stereoselective Synthesis of MLN4924, an Inhibitor of NEDD8-Activating Enzyme", *J. Org. Chem.* 76(9):3557-3561, Mar. 21, 2011.
Nam, S. K. et al., "A New Preparation Process for NAE inhibitor, MLN 4924", in *241st American Chemical Society National Meeting & Exposition Chemistry of Natural Resources On-site Program*, American Chemical Society, Anaheim, Calif., USA, Mar. 27-31, 2011, 3 Pages.

* cited by examiner

*Primary Examiner* — Jeffrey H Murray
(74) *Attorney, Agent, or Firm* — Seed IP Law Group PLLC

(57) ABSTRACT

The present invention relates to a method for preparation of MLN4924 as an E1 activating inhibitor, and more specifically, to a method for efficient and stereoselective preparation of MLN4924 by means of key steps involving stereoselective reduction of cyclopentenone with isopropylidene, regioselective cleavage of isopropylidene moiety, and synthesis of cyclic sulfate.

16 Claims, No Drawings

PREPARATION METHOD OF MLN4924 AS AN E1 ACTIVATING INHIBITOR

FIELD OF THE INVENTION

The present invention relates to a method for preparation of MLN4924 as an E1 activating inhibitor. More specifically, the present invention relates to a method for efficient and stereoselective preparation of MLN4924 by means of key steps involving stereoselective reduction of cyclopentenone with isopropylidene, regioselective cleavage of isopropylidene, and synthesis of cyclic sulfate.

BACKGROUND

The ubiquitin-proteasome system (UPS) plays an important role in the conjugation pathway, which appends ubiquitin to the substrate proteins targeted for regulated degradation (Hershko, A. Cell Death Differ. 2005, 12, 1191-1197). Such ubiquitinylation pathway is composed of three enzymatic steps comprising ubiquitin-activating enzyme (E1), ubiquitin-conjugating enzyme (E2) (UBC) and ubiquitin-protein isopeptide ligase (E3) (Hershko, A. et al., Annu. Rev. Biochem. 1998, 67, 425-479). Another pathway similar to the ubiquitinylation pathway that employs the ubiquitin-like protein NEDD8 (neural precursor cell-expressed developmentally down-regulated 8) has also been identified (Kerscher, O. et al., Annu. Rev. Cell Dev. Biol. 2006, 22, 159-180; Gong, L. et al., J. Biol. Chem. 1999, 274, 12036-12042). In the first step, NEDD8 is activated by E1 enzyme (NEDD8 activating enzyme, NAE). In the second step, NEDD8 is transferred to E2 enzyme (UBC12). Subsequently, E2 is conjugated to the substrate protein targeted for degradation. In this pathway, NAE plays an essential role in regulating the activity of a cullin-RING subtype (really interesting new gene) of ubiquitin ligases, whose substrates play important roles in the cellular processes associated with cancer cell growth (Pan, Z. Q. et al., Oncogene 2004, 23, 1985-1997). Therefore, NAE has been contemplated as a new target for the development of novel anticancer agents.

MLN4924 is a potent and selective inhibitor of NEDD8 activating enzyme (NAE) and is currently being investigated in phase I clinical trials as an anticancer agent for both solid tumor and hematological malignancies. MLN4924 mimics adenosine 5'-monophosphate (AMP), which is a tight binding product of NAE reaction (Haas, A. L. et al., J. Biol. Chem. 1982, 257, 10329-10337; Bohnsack, R. N. et al., J. Biol. Chem. 2003, 278, 26823-26830). MLN4924 inhibits the NAE pathway in cells, which results in S-phase defect, DNA damage and apoptosis (Soucy, T. A. et al., Nature 2009, 458, 732-737). MLN4924 also inhibits NAE pathway to induce DNA damage in mouse bearing human HCT-116 tumor xenografts (Soucy, T. A. et al., Nature 2009, 458, 732-737).

However, despite its potent anticancer activity MLN4924 has been little studied with regard to the method for synthesis thereof. Therefore, in consideration of the importance of said compound it is very important to develop the method for stereoselectively and efficiently synthesizing MLN4924 with a good overall yield under mild conditions.

Thus, the present inventors have studied under taking the above-mentioned aspects into consideration, and found that MLN4924 can be efficiently and stereoselectively prepared by means of key steps involving stereoselective reduction of cyclopentenone with isopropylidene, regioselective cleavage of isopropylidene moiety, and synthesis of cyclic sulfate, resulting in the completion of the present invention.

SUMMARY OF INVENTION

The object of the present invention is to provide a method for efficiently and stereoselectively preparing MLN4924.

DETAILED DESCRIPTION OF INVENTION

To solve the above subject, the present invention provides a method for preparation of a compound represented by the following formula 1, which method comprises the following steps:

preparing a compound represented by the following formula 5 by hydrogenating a compound represented by the following formula 6 in the presence of a palladium catalyst (step 1);

preparing a compound represented by the following formula 7 by reacting the compound of formula 5 with $NaBH_4$ and $CeCl_3 \cdot 7H_2O$ (step 2);

preparing a compound represented by the following formula 4 by reacting the compound of formula 7 with trimethyl aluminum (step 3);

preparing a compound represented by the following formula 3 by reacting the compound of formula 4 with thionyl chloride to prepare a cyclic sulfite compound, which is then oxidized by means of $RuCl_3$ and $NaIO_4$ (step 4);

preparing a compound represented by the following formula 8 by reacting the compound of formula 3 with $N^6$-indanyl-7-deazaadenine followed by subjecting to hydrolysis (step 5);

preparing a compound represented by the following formula 9 by reacting the compound of formula 8 with phenyl chlorothionoformate to prepare a thiocarbonate compound, which is then reacted with n-$Bu_3$SnH in the presence of AIBN (step 6);

preparing a compound represented by the following formula 10 by reacting the compound of formula 9 with pyridine.HF (step 7);

preparing a compound represented by the following formula 11 by reacting the compound of formula 10 with chlorosulfonamide (step 8); and preparing a compound represented by the following formula 1 by reacting the compound of formula 11 with TFA (step 9):

[Formula 1]

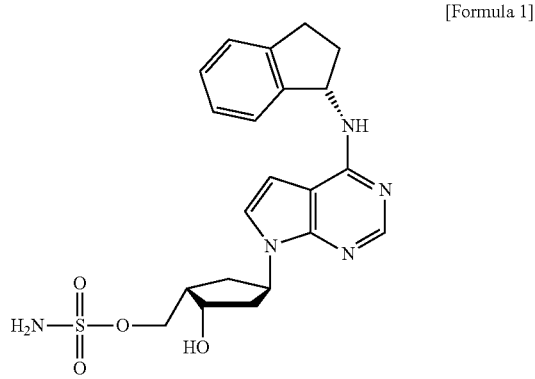

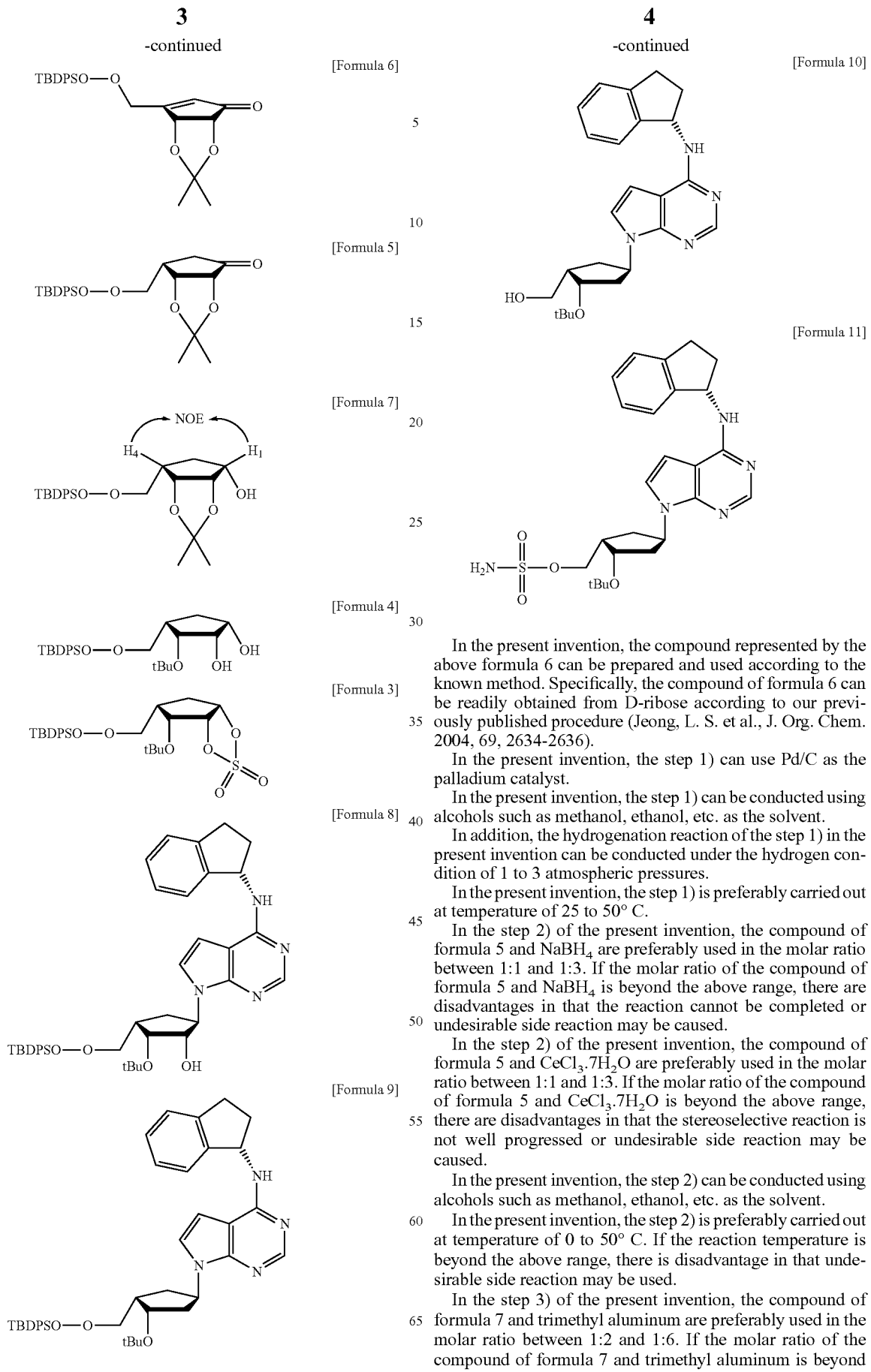

In the present invention, the compound represented by the above formula 6 can be prepared and used according to the known method. Specifically, the compound of formula 6 can be readily obtained from D-ribose according to our previously published procedure (Jeong, L. S. et al., J. Org. Chem. 2004, 69, 2634-2636).

In the present invention, the step 1) can use Pd/C as the palladium catalyst.

In the present invention, the step 1) can be conducted using alcohols such as methanol, ethanol, etc. as the solvent.

In addition, the hydrogenation reaction of the step 1) in the present invention can be conducted under the hydrogen condition of 1 to 3 atmospheric pressures.

In the present invention, the step 1) is preferably carried out at temperature of 25 to 50° C.

In the step 2) of the present invention, the compound of formula 5 and NaBH$_4$ are preferably used in the molar ratio between 1:1 and 1:3. If the molar ratio of the compound of formula 5 and NaBH$_4$ is beyond the above range, there are disadvantages in that the reaction cannot be completed or undesirable side reaction may be caused.

In the step 2) of the present invention, the compound of formula 5 and CeCl$_3$.7H$_2$O are preferably used in the molar ratio between 1:1 and 1:3. If the molar ratio of the compound of formula 5 and CeCl$_3$.7H$_2$O is beyond the above range, there are disadvantages in that the stereoselective reaction is not well progressed or undesirable side reaction may be caused.

In the present invention, the step 2) can be conducted using alcohols such as methanol, ethanol, etc. as the solvent.

In the present invention, the step 2) is preferably carried out at temperature of 0 to 50° C. If the reaction temperature is beyond the above range, there is disadvantage in that undesirable side reaction may be used.

In the step 3) of the present invention, the compound of formula 7 and trimethyl aluminum are preferably used in the molar ratio between 1:2 and 1:6. If the molar ratio of the compound of formula 7 and trimethyl aluminum is beyond the above range, there are disadvantages in that the reaction cannot be completed or undesirable side reaction may be caused.

In the present invention, the step 3) can be conducted using methylene chloride, chloroform, dichloroethane, etc. as the solvent.

In the present invention, the step 3) is preferably carried out at temperature of 0 to 30° C. If the reaction temperature is beyond the above range, there is disadvantage in that undesirable side reaction may be used.

In the step 4) of the present invention, the compound of formula 4 and thionyl chloride are preferably used in the molar ratio between 1:1 and 1:3. If the molar ratio of the compound of formula 4 and thionyl chloride is beyond the above range, there are disadvantages in that the reaction cannot be completed or undesirable side reaction may be caused.

In the present invention, the reaction of the compound of formula 4 with thionyl chloride according to the step 4) can be conducted using methylene chloride, chloroform, benzene, toluene, etc. as the solvent.

In the present invention, the reaction of the compound of formula 4 with thionyl chloride according to the step 4) is preferably carried out at temperature of 0 to 30° C. If the reaction temperature is beyond the above range, there are disadvantages in that the reaction cannot be completed or undesirable side reaction may be caused.

In the step 4) of the present invention, the cyclic sulfite compound and $RuCl_3$ are preferably used in the molar ratio between 1:0.2 and 1:1. If the molar ratio of the cyclic sulfite compound and $RuCl_3$ is beyond the above range, there are disadvantages in that the reaction cannot be completed or undesirable side reaction may be caused.

In the step 4) of the present invention, the cyclic sulfite compound and $NaIO_4$ are preferably used in the molar ratio between 1:1 and 1:3. If the molar ratio of the cyclic sulfite compound and $NaIO_4$ is beyond the above range, there are disadvantages in that the reaction cannot be completed or undesirable side reaction may be caused.

In the present invention, the reaction of the cyclic sulfite compound with $RuCl_3$ and $NaIO_4$ according to the step 4) can be conducted using carbon tetrachloride, acetonitrile, water, or a mixture thereof as the solvent.

In the present invention, the reaction of the cyclic sulfite compound with $RuCl_3$ and $NaIO_4$ according to the step 4) is preferably carried out at temperature of 0 to 30° C. If the reaction temperature is beyond the above range, there are disadvantages in that the reaction cannot be completed or undesirable side reaction may be caused.

In the step 5) of the present invention, the compound of formula 3 and $N^6$-indanyl-7-deazaadenine are preferably used in the molar ratio between 1:1 and 1:3. If the molar ratio of the compound of formula 3 and $N^6$-indanyl-7-deazaadenine is beyond the above range, there are disadvantages in that the reaction cannot be completed or undesirable side reaction may be caused.

In the present invention, the hydrolysis according to the step 5) can be carried out by means of hydrochloric acid, sulfuric acid or nitric acid.

In the present invention, the step 5) can be conducted using THF, 1,4-dioxane, dimethylformamide, etc. as the solvent.

In the present invention, the step 5) is preferably carried out at temperature of 50 to 100° C. If the reaction temperature is beyond the above range, there are disadvantages in that the reaction cannot be completed or undesirable side reaction may be caused.

In the step 6) of the present invention, the compound of formula 8 and phenyl chlorothionoformate are preferably used in the molar ratio between 1:1 and 1:5. If the molar ratio of the compound of formula 8 and phenyl chlorothionoformate is beyond the above range, there are disadvantages in that the reaction cannot be completed or undesirable side reaction may be caused.

In the present invention, the reaction of the compound of formula 8 with phenyl chlorothionoformate according to the step 6) can be conducted using methylene chloride, chloroform, benzene, toluene, etc. as the solvent.

In the present invention, the reaction of the compound of formula 8 with phenyl chlorothionoformate according to the step 6) is preferably carried out at temperature of 0 to 50° C. If the reaction temperature is beyond the above range, there are disadvantages in that the reaction cannot be completed or undesirable side reaction may be caused.

In the step 6) of the present invention, the thiocarbonate compound and AIBN are preferably used in the molar ratio between 1:1 and 1:3. If the molar ratio of the thiocarbonate compound and AIBN is beyond the above range, there are disadvantages in that the reaction cannot be completed or undesirable side reaction may be caused.

In the step 6) of the present invention, the thiocarbonate compound and $n$-$Bu_3SnH$ are preferably used in the molar ratio between 1:1 and 1:4. If the molar ratio of the thiocarbonate compound and $n$-$Bu_3SnH$ is beyond the above range, there are disadvantages in that the reaction cannot be completed or undesirable side reaction may be caused.

In the present invention, the reaction of the thiocarbonate compound with $n$-$Bu_3SnH$ in the presence of AIBN according to the step 6) can be conducted using toluene, benzene, etc. as the solvent.

In the present invention, the reaction of the thiocarbonate compound with $n$-$Bu_3SnH$ in the presence of AIBN according to the step 6) is preferably carried out at temperature of 50 to 110° C. If the reaction temperature is beyond the above range, there are disadvantages in that the reaction cannot be completed or undesirable side reaction may be caused.

In the step 7) of the present invention, the compound of formula 9 and pyridine.HF are preferably used in the molar ratio between 1:1 and 1:10. If the molar ratio of the compound of formula 9 and pyridine.HF is beyond the above range, there are disadvantages in that the reaction cannot be completed or undesirable side reaction may be caused.

In the present invention, the step 7) can be conducted using THF, pyridine or a mixture thereof as the solvent.

In the present invention, the step 7) is preferably carried out at temperature of 0 to 30° C. If the reaction temperature is beyond the above range, there are disadvantages in that the reaction cannot be completed or undesirable side reaction may be caused.

In the step 8) of the present invention, the compound of formula 10 and chlorosulfonamide are preferably used in the molar ratio between 1:2 and 1:5. If the molar ratio of the compound of formula 10 and chlorosulfonamide is beyond the above range, there are disadvantages in that the reaction cannot be completed or undesirable side reaction may be caused.

In the present invention, the step 8) can be conducted using acetonitrile, THF, etc. as the solvent.

In the present invention, the step 8) is preferably carried out at temperature of 0 to 30° C. If the reaction temperature is beyond the above range, there are disadvantages in that the reaction cannot be completed or undesirable side reaction may be caused.

In the step 9) of the present invention, the compound of formula 11 and TFA are preferably used in the molar ratio between 1:10 and 1:100. If the molar ratio of the compound of formula 11 and TFA is beyond the above range, there are disadvantages in that the reaction cannot be completed or undesirable side reaction may be caused.

In the present invention, the step 9) is preferably carried out at temperature of 0 to 30° C. If the reaction temperature is beyond the above range, there are disadvantages in that the reaction cannot be completed or undesirable side reaction may be caused.

The retrosynthetic analysis of MLN4924 (1), as the final desired nucleoside, is shown in the following.

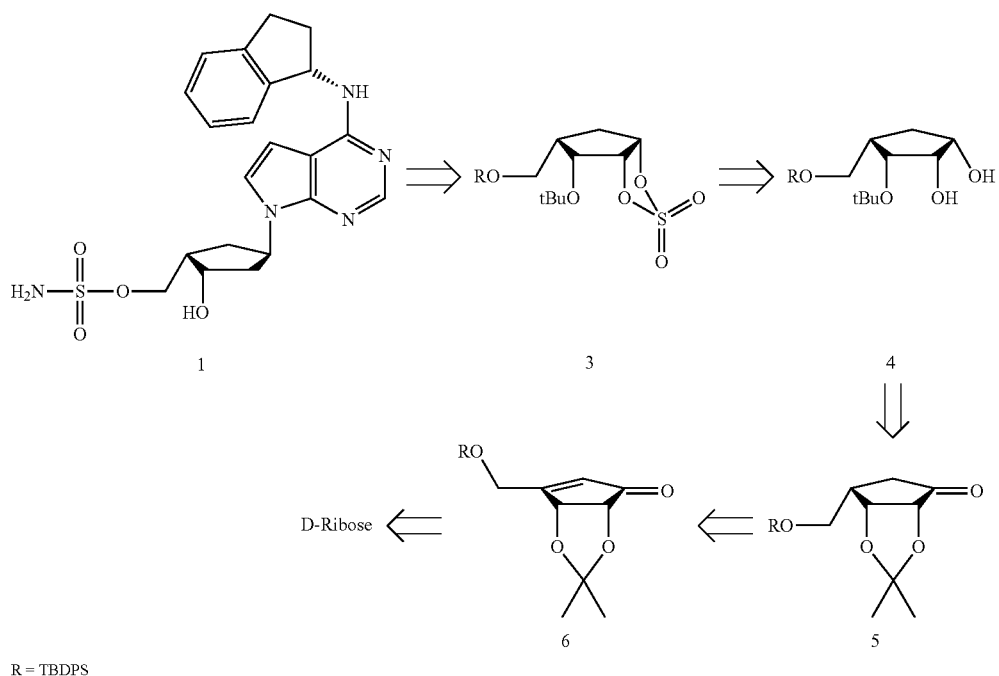

R = TBDPS

MLN 4924 (1) can be synthesized by condensing cyclic sulfate 3 as the glycosyl donor with a purine base. The glycosyl donor 3 can be produced from diol 4, which in turn can be obtained from cyclopentanone 5 via a stereoselective reduction and a regioselective cleavage of the isopropylidene moiety. The cyclopentanone 5 can be synthesized from cyclopentenone 6 by stereoselective reduction. The intermediate cyclopentenone 6 can be easily derived from D-ribose according to our previously published procedure (Jeong, L. S. et al., J. Org. Chem. 2004, 69, 2634-2636).

The synthetic route for the glycosyl donor 3 is shown in the following scheme 1.

[Scheme 1]

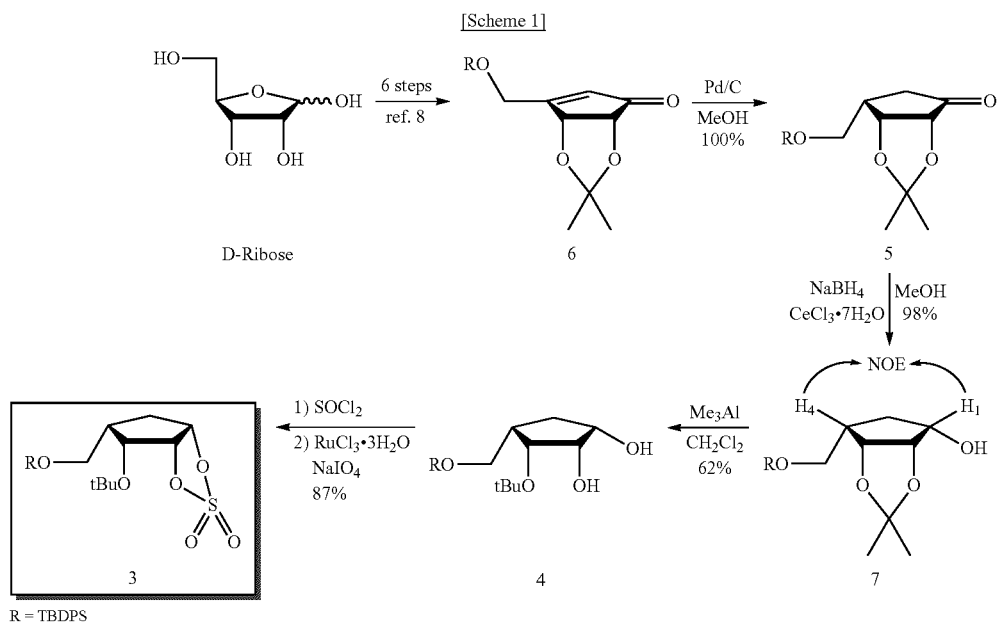

R = TBDPS

In the present invention, the synthesis of the glycosyl donor 3 begins with the known cyclopentenone 6, which was efficiently synthesized from D-ribose in 6 steps (Jeong, L. S. et al., J. Org. Chem. 2004, 69, 2634-2636) (Scheme 1). Catalytic hydrogenation of cyclopentenone 6 with 10% Pd/C gave cyclopentanone 5 in quantitative yield as a single stereoisomer, due to the incorporation of hydrogen from the convex side of the molecule. Luche reduction of ketone 5 with NaBH$_4$ and CeCl$_3$.7H$_2$O (Luche, J.-L. J. Am. Chem. Soc. 1978, 100, 2226-2227) afforded alcohol 7 as a single diastereomer. The configuration of the newly created asymmetric center in 7 was easily confirmed by NOESY experiments. The NOE effect between H-1 and H-4 in the compound 7 was observed, indicating a cis relationship. Regioselective cleavage of isopropyliden present in the compound 7 was achieved by treatment with trimethylaluminum, which gave diol 4 (Takano, S. et al., Tetrahedron Lett. 1988, 29, 1823-1824; Siddiqui, M. A. et al., Nucleosides Nucleotides 1996, 15, 235-250). Diol 4 was converted to cyclic sulfate 3 by treatment with thionyl chloride and subsequent oxidation with RuCl$_3$ and NaIO$_4$ (Lohray, B. B, Synthesis 1992, 1035-1052; Lohray, B. B. et al., Adv. Heterocycl. Chem. 1997, 68, 89-180; Byun, H.-S. et al., Tetrahedron 2000, 56, 7051-7091).

The synthetic route for the final desired compound, MLN4924 (1) is shown in the following scheme 2.

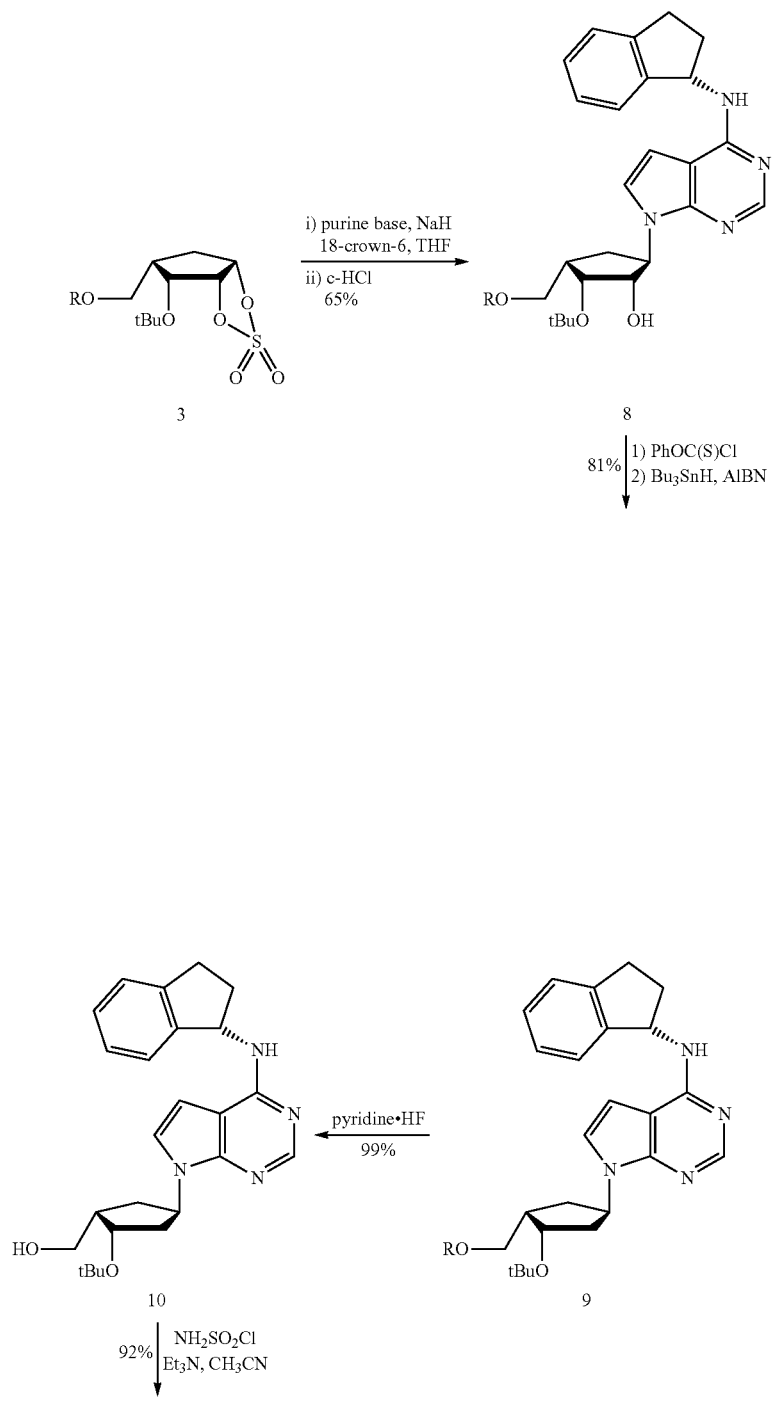

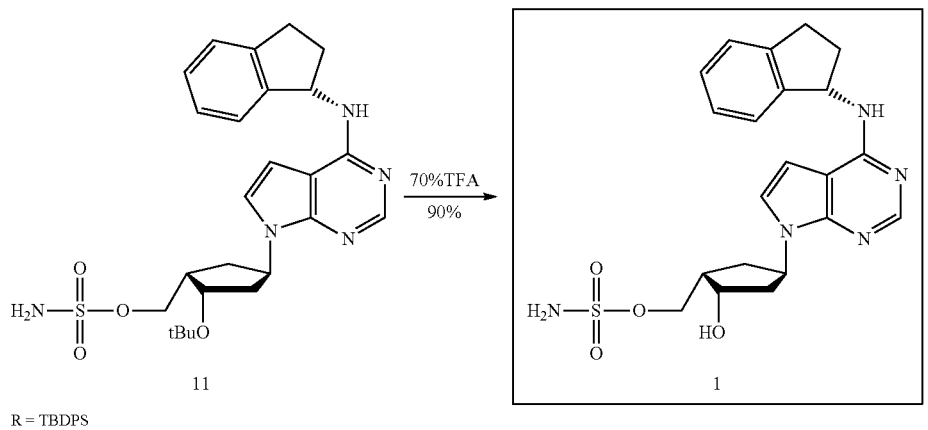

R = TBDPS

To complete the synthesis of the final desired compound MLN4924 (1), glycosyl donor 3 was reacted with the anion of $N^6$-indanyl-7-deazaadenine in THF (Scheme 2). After hydrolyzing the resulting sulfate, the desired $N^9$-isomer 8 was obtained as a single diastereomer (65%) (Jeong, L. S. et al., Org. Lett. 2006, 8, 5081-5083). Said $N^9$-isomer was treated with phenyl chlorothionoformate, and then further reacted with n-$Bu_3SnH$ in the presence of AIBN to obtain the 2'-deoxygenated derivative 9. The compound 9 was treated with pyridine.HF to obtain the 5'-hydroxyl compound 10, which was then treated with chlorosulfonamide to obtain the 5'-sulfonamido derivative 11. The tert-butyl group in the compound 11 was removed with 70% TFA to afford MLN4924 (1) in the yield of 90%.

In summary, the present inventors provided the efficient stereoselective synthesis of MLN4924, a compound in phase I clinical trial as an anticancer agent. In the present invention, MLN4924 was stereoselectively prepared under mild conditions. In particular, the key steps of the synthetic procedure include stereoselective reduction of cyclopentenone with isopropylidene, regioselective cleavage of the isopropylidene group, and position-selective substitution of cyclic sulfate moiety. All reactions employed in the present invention are expected to be very useful for the synthesis of new carbocyclic nucleosides.

The present invention has a superior effect to provide a method capable of efficiently and stereoselectively preparing MLN4924 I high yield, which method employs stereoselective reduction of cyclopentenone with isopropylidene, regioselective cleavage of the isopropylidene group, and synthesis of cyclic sulfate as key steps.

Hereinafter, the present invention is specifically illustrated with reference to the following examples. However, it should be understood that the following examples are intended only to help understanding of the present invention, but the scope of the present invention is not limited by those examples in any manner

EXAMPLES

Example 1

Preparation of MLN4924

Step 1: Preparation of 6-(tert-butyl-diphenyl-silanyloxymethyl)-2,2-dimethyl-tetrahydro-cyclopenta[1,3]dioxol-4-one (Compound 5)

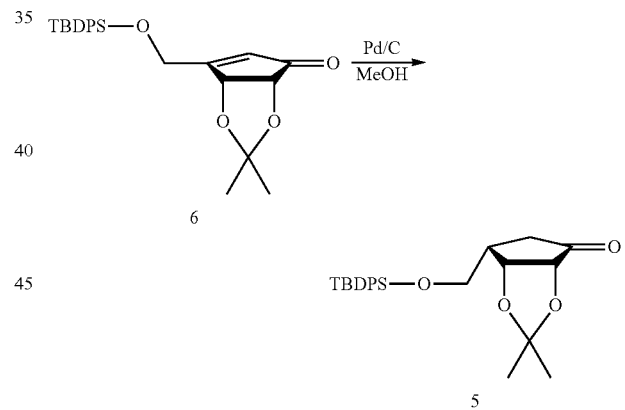

To a suspension of the compound 6 (20.0 g, 47.1 mmol) in methanol (400 ml) was added 10% palladium on activated carbon (1.0 g), and the mixture was stirred at room temperature overnight under $H_2$ atmosphere. After filtration of the reaction mixture, the solvent was removed and the residue was dissolved in methylene chloride and then filtered through short pad silica gel. Then, the solvent was evaporated to give the compound 5 (20.1 g, 100%) as a colorless syrup.

$[\alpha]^{20}_D$ −28.32 (c 1.49, MeOH); HR-MS (ESI): m/z calcd for $C_{25}H_{32}NaO_4Si$ $[M+Na]^+$ 447.1968, Found 447.1956; $^1H$ NMR (400 MHz, $CDCl_3$) δ 7.69 (m, 4 H), 7.40 (m, 6 H), 4.84 (t, J=4.4 Hz, 1 H), 4.22 (dd, J=1.2, 4.8 Hz, 1 H), 3.96 (dd, J=8.0, 10.0 Hz, 1 H), 3.82 (dd, J=6.8, 10.0 Hz, 1 H), 2.37 (m, 1 H), 2.30 (ddd, J=1.2, 8.4, and 18.4 Hz, 1 H), 2.20 (ddd, J=1.2, 12.0, and 18.4 Hz, 1 H), 1.37 (s, 3 H), 1.35 (s, 3 H), 1.06 (s, 9 H); $^{13}C$ NMR (100 MHz, $CDCl_3$) δ 112.6, 80.5, 77.6, 77.2, 76.9, 63.6, 38.1, 36.9, 27.1, 27.02, 27.01, 25.3, 19.5; Anal. Calcd for $C_{25}H_{32}O_4Si$: C, 70.72; H, 7.60. Found: C, 70.79; H, 7.75.

Step 2: Preparation of 6-(tert-butyl-diphenyl-silanyloxymethyl)-2,2-dimethyl-tetrahydro-cyclopenta[1,3]dioxol-4-ol (Compound 7)

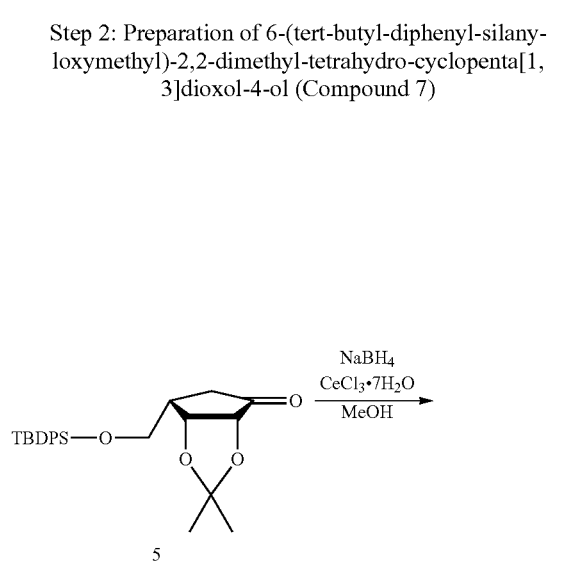

To a suspension of the compound 5 (20.1 g, 47.1 mmol) in methanol (500 ml) were added sodium borohydride (2.17 g, 57.4 mmol) and cerium (III) chloride heptahydrate (21.3 g, 57.2 mmol) at 0° C., and the mixture was stirred at room temperature for 30 min. After the solvent was removed, the residue was partitioned between ethyl acetate and water. The organic layer was then washed with brine, dried with anhydrous MgSO$_4$, filtered, and evaporated. The residue was purified by silica gel column chromatography (hexane/ethyl acetate=5/1) to give the compound 7 (20.86 g, 98%) as a colorless syrup.

$[\alpha]^{20}_D$ +34.55 (c 0.55, MeOH); HR-MS (ESI): m/z calcd for $C_{25}H_{34}NaO_4Si$ [M+Na]$^+$: 449.2124; Found: 449.2110; $^1$H NMR (400 MHz, CDCl$_3$) δ 7.69 (m, 4 H), 7.39 (m, 6 H), 4.62 (t, J=5.6 Hz, 1 H), 4.44 (t, J=5.6 Hz, 1 H), 3.89 (dd, J=6.0, 7.6 Hz, 1H), 3.84 (m, 1 H), 3.68 (dd, J=6.4, 10.0 Hz, 1 H), 1.91 (m, 2 H), 1.26 (m, 1 H), 1.42 (s, 3 H), 1.33 (s, 3 H), 1.05 (s, 9 H); $^{13}$C NMR (100 MHz, CDCl$_3$) δ 135.9, 135.8, 134.2, 134.1, 129.8, 129.7, 127.8, 127.7, 110.6, 79.4, 78.9, 77.6, 77.2, 76.9, 72.5, 62.9, 41.6, 33.4, 27.0, 25.9, 27.0, 25.9, 24.4, 19.5; Anal. Calcd for $C_{25}H_{34}O_4Si$: C, 70.38; H, 8.03. Found: C, 70.41; H, 8.08.

Step 3: Preparation of 3-tert-butoxy-4-(tert-butyl-diphenyl-silanyloxymethyl)-cyclopentane-1,2-diol (Compound 4)

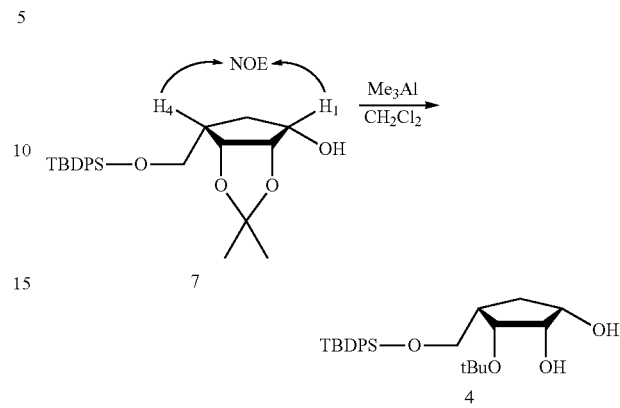

To a solution of the compound 7 (20.86 g, 47.12 mmol) in methylene chloride was added trimethylaluminum (2.0 M in toluene, 132.1 ml) at 0° C., and the mixture was stirred at room temperature for 2 days. The mixture was cooled to 0° C., slowly quenched with an aqueous saturated ammonium chloride solution, filtered, and evaporated. The residue was partitioned between ethyl acetate and water. The organic layer was washed with brine, dried with anhydrous MgSO$_4$, filtered, and evaporated. The residue was purified by silica gel column chromatography (hexane/ethyl acetate=2/1) to give the compound 4 (13.42 g, 62%) as a colorless syrup.

$[\alpha]^{20}_D$ +3.30 (c 0.55, MeOH); HR-MS (ESI): m/z calcd for $C_{26}H_{38}NaO_4Si$ [M+Na]$^+$: 465.2437; Found: 465.2423; $^1$H NMR (400 MHz, CDCl$_3$) δ 7.70 (m, 4 H), 7.41 (m, 6 H), 4.05 (dd, J=4.4, 7.2 Hz, 1 H), 3.93 (m, 1 H), 3.72 (m, 2 H), 3.59 (dd, J=3.6, 12.0 Hz, 2 H), 2.70 (d, J=20.8 Hz, 1 H), 2.10 (m, 2 H), 1.60 (m, 1 H), 1.20 (s, 9 H), 1.06 (s, 9 H); $^{13}$C NMR (100 MHz, CDCl$_3$) δ 135.9, 133.5, 130.0, 129.9, 127.9, 127.9, 77.6, 77.2, 76.9, 74.9, 73.8, 72.7, 72.1, 63.3, 42.1, 34.0, 28.5, 27.0, 19.4; Anal. Calcd for $C_{26}H_{38}O_4Si$: C, 70.55; H, 8.65. Found: C, 70.61; H, 8.70.

Step 4: Preparation of (4-tert-butoxy-2,2-dioxo-tetrahydro-2-yl-6-cyclopenta[1,3,2]-dioxathiol-5-yl-methoxy)-tert-butyl-diphenyl-silane (Compound 3)

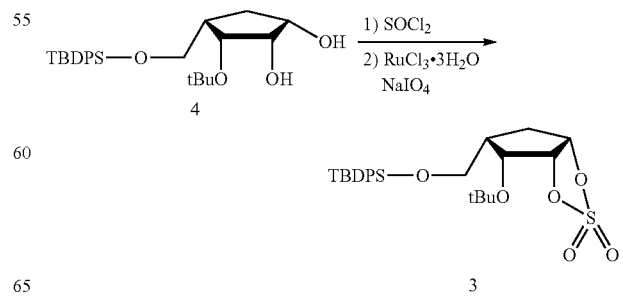

To a solution of the compound 4 (13.42 g, 30.3 mmol) in methylene chloride were added triethyl amine (14.5 ml, 101.0 mmol) and thionyl chloride (3.7 ml, 47.4 mmol) at 0° C., and the reaction mixture was stirred at 0° C. for 10 minutes. The reaction mixture was partitioned between methylene chloride and water. The organic layer was washed with brine, dried with anhydrous MgSO$_4$, filtered, and evaporated. The residue was purified by silica gel column chromatography (hexane/ethyl acetate=6/1) to give the cyclic sulfite (14.37 g, 97%) as a white foam.

$[\alpha]^{20}_D$ +20.00 (c 0.05, MeOH); HR-MS (ESI): m/z calcd for C$_{26}$H$_{36}$NaO$_5$SSi [M+Na]$^+$: 511.1950; Found: 511.1929; $^1$H NMR (400 MHz, CDCl$_3$) δ 7.64 (m, 4 H), 7.40 (m, 6 H), 5.23 (m, 1 H), 5.04 (dd, J=4.4, 6.0 Hz, 1 H), 4.01 (t, J=4.8 Hz, 1 H), 3.68 (dd, J=3.6, 10.4 Hz, 1 H), 3.56 (dd, J=8.0, 10.4 Hz, 1 H), 2.07 (m, 2 H), 1.96 (m, 1 H), 1.14 (s, 9 H), 1.05 (s, 9 H); $^{13}$C NMR (100 MHz, CDCl$_3$) δ 135.8, 135.7, 133.9, 133.8, 129.9, 129.9, 127.9, 127.8, 85.7, 83.2, 77.6, 77.2, 76.9, 75.0, 71.1, 62.7, 44.7, 31.4, 28.5, 27.1, 19.4; Anal. Calcd for C$_{26}$H$_{36}$O$_5$SSi: C, 63.90; H, 7.42; S, 6.56. Found: C, 63.94; H, 7.45; S, 6.61.

To a solution of the cyclic sulfite obtained above (14.37 g, 29.4 mmol) in the mixture of carbon tetrachloride, acetonitrile and water (1:1:1.5, 210 ml) were added sodium metaperiodate (18.56 g, 56.4 mmol) and ruthenium chloride (1.72 g, 8.25 mmol), and the reaction mixture was stirred at room temperature for 10 minutes. The reaction mixture was partitioned between methylene chloride and water. The organic layer was washed with brine, dried with anhydrous MgSO$_4$, filtered, and evaporated. The residue was purified by silica gel column chromatography (hexane/ethyl acetate=4/1) to give the compound 3 (13.36 g, 90%) as a white solid.

mp 101-104° C.; $[\alpha]^{20}_D$ -80.00 (c 0.05, MeOH); HR-MS (ESI): m/z calcd for C$_{26}$H$_{36}$NaO$_6$SSi [M+Na]$^+$: 527.1900; Found: 527.1881; $^1$H NMR (400 MHz, CDCl$_3$) δ 7.64 (m, 4 H), 7.41 (m, 6 H), 5.13 (m, 1 H), 4.83 (dd, J=4.4, 6.8 Hz, 1 H), 4.13 (t, J=4.0 Hz, 1 H), 3.92 (dd, J=6.4, 10.4 Hz, 1 H), 3.69 (dd, J=5.2, 10.4 Hz, 1 H), 2.11 (m, 2H), 2.02 (m, 1 H), 1.15 (s, 9 H), 1.05 (s, 9 H); $^{13}$C NMR (100 MHz, CDCl$_3$) δ 135.7, 135.0, 133.8, 133.7, 130.0, 128.0, 127.9, 83.5, 82.2, 77.6, 77.2, 76.9, 75.4, 70.4, 70.4, 62.2, 43.9, 31.3, 28.2, 27.1, 26.8, 19.4; Anal. Calcd for C$_{26}$H$_{36}$O$_6$SSi: C, 61.87; H, 7.19; S, 6.35. Found: C, 61.91; H, 7.14; S, 6.30.

Step 5: Preparation of 2-tert-butoxy-3-(tert-butyl-diphenyl-silanyloxymethyl)-5-[4-(indan-1-ylamino)-pyrrolo[2,3-d]pyrimidin-7-yl]-cyclopentanol (Compound 8)

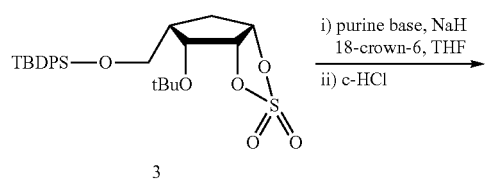

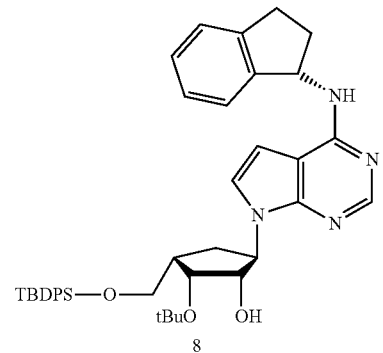

A suspension of N$^6$-indanyl-7-deazaadenine (8.80 g, 35.2 mmol), sodium hydride (1.38 g, 45.7 mmol) and 18-crown-6 (9.11 g, 45.7 mmol) in THF (200 ml) was stirred at 80° C. To the reaction mixture was added a solution for the compound 3 (13.36 g, 26.5 mmol) in THF (150 ml), and the stirring was continued at 80° C. overnight. The reaction mixture was cooled down to 0° C., and conc. HCl was added slowly until pH reaches 1~2. Then the reaction mixture was further stirred at 80° C. for 2 hours. After neutralized with saturated aqueous NaHCO$_3$ solution, the reaction mixture was partitioned between ethyl acetate and water. The organic layer was washed with brine, dried with anhydrous MgSO$_4$, filtered, and evaporated. The residue was purified by silica gel column chromatography (hexane/ethyl acetate=2/1) to give the compound 8 (11.62 g, 65%) as a white foam.

UV (CH$_2$Cl$_2$) λ$_{max}$ 272.5 nm; $[\alpha]^{20}_D$ -8.89 (c 0.45, MeOH); HR-MS (ESI): m/z calcd for C$_{41}$H$_{51}$N$_4$O$_3$Si [M+H]$^+$: 675.3730; Found: 675.3717; $^1$H NMR (400 MHz, CDCl$_3$) δ 8.38 (s, 1 H), 7.70 (m, 4 H), 7.41 (m, 6 H), 6.92 (d, J=3.6 Hz, 1 H), 6.29 (d, J=3.2 Hz, 1 H), 5.91 (dd, J=7.6, 14.8 Hz, 1 H), 5.14 (br d, J=6.8 Hz, 1 H), 4.77 (m, 1H), 4.36 (t, J=6.0 Hz, 1 H), 4.22 (dd, J=5.2, 10.8 Hz, 1 H), 3.84 (dd, J=5.6, 10.4 Hz, 1H), 3.73 (dd, J=8.4, 10.4 Hz, 1 H), 3.37 (d, J=5.6 Hz, 1 H), 3.06 (m, 1 H), 2.95 (m, 1H), 2.75 (m, 1 H), 2.75 (m, 1 H), 2.58 (m, 1 H), 2.38 (m, 1 H), 2.15 (m, 1 H), 1.98 (m, 1H), 1.65 (s, 1 H), 1.55 (s, 1 H), 1.16 (s, 9 H), 1.07 (s, 9 H); $^{13}$C NMR (100 MHz, CDCl$_3$) δ 156.4, 151.8, 150.3, 144.1, 143.8, 135.9, 134.0, 129.9, 128.2, 127.9, 127.9, 127.0, 125.1, 124.4, 123.3, 103.8, 97.4, 77.8, 77.6, 77.2, 76.9, 74.9, 72.4, 63.5, 62.1, 56.3, 43.9, 34.9, 30.5, 30.5, 28.5, 27.2, 19.5; Anal. Calcd for C$_{41}$H$_{50}$N$_4$O$_3$Si: C, 72.96; H, 7.47; N, 8.30. Found: C, 73.01; H, 7.45; N, 8.36.

Step 6: Preparation of {7-[3-tert-butoxy-4-(tert-bu-
tyl-diphenyl-silanyloxymethyl)-cyclopentyl]-7H-
pyrrolo[2,3-d]pyrimidin-4-yl}-indan-1-yl-amine
(Compound 9)

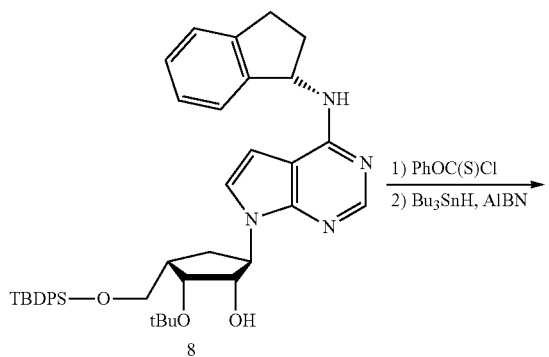

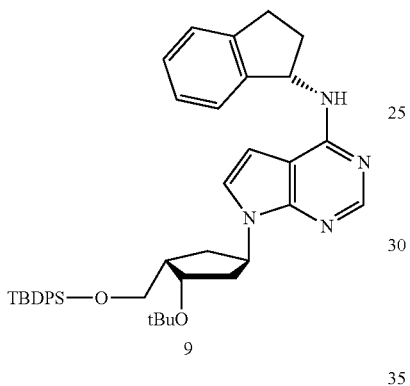

To a solution of the compound 8 (11.62 g, 17.2 mmol) in methylene chloride (300 ml) were added N,N-dimethylaminopyridine (5.64 g, 51.6 mmol) and phenyl chlorothionocarbonate (4.3 ml, 34.4 mmol), and the reaction mixture was stirred at room temperature overnight. After the solvent was removed, the residue was purified by silica gel column chromatography (hexane/ethyl acetate=6/1) to give the thiocarbonate (13.82 g, 99%) as a white foam.

UV (MeOH) $\lambda_{max}$ 271.50 nm; $[\alpha]^{20}_D$ +10.00 (c 0.15, MeOH); HR-MS (ESI): m/z calcd for $C_{48}H_{55}N_4O_4SSi$ [M+H]$^+$: 811.3713; Found: 811.3687; $^1$H NMR (400 MHz, CDCl$_3$) δ 8.36 (s, 1 H), 7.61 (dd, J=1.6, 7.6 Hz, 4 H), 7.34 (m, 5 H), 7.26 (m, 4 H), 7.18 (m, 6 H), 6.86 (s, 1 H), 6.25 (d, J=3.2 Hz, 1 H), 6.00 (dd, J=3.2, 8.4 Hz, 1 H), 5.83 (d, J=6.8 Hz, 1 H), 5.19 (m, 1 H), 5.07 (br s, 1 H), 4.48 (t, J=3.6 Hz, 1 H), 3.82 (dd, J=7.2, 10.4 Hz, 1 H), 3.52 (dd, J=7.2, 10.0 Hz, 1 H), 2.99 (m, 1 H), 2.88 (m, 2 H), 2.69 (m, 2 H), 2.18 (dd, J=11.2, 13.6 Hz, 1 H), 1.94 (m, 2 H), 1.12 (s, 9 H), 0.98 (s, 9 H); $^{13}$C NMR (100 MHz, CDCl$_3$) δ 194.9, 153.5, 152.1, 143.9, 135.9, 135.8, 134.1, 129.9, 129.6, 128.3, 127.9, 127.0, 126.7, 125.1, 124.6, 123.2, 122.0, 87.9, 77.6, 77.2, 76.9, 74.6, 70.4, 63.5, 57.3, 42.8, 35.0, 30.7, 30.5, 29.9, 28.7, 27.1, 19.4; Anal. Calcd for $C_{48}H_{54}N_4O_4SSi$: C, 71.08; H, 6.71; N, 6.91; S, 3.95. Found: C, 71.14; H, 6.75; N, 6.95; S, 4.01.

To a solution of the thiocarbonate obtained above (13.82 g, 17.0 mmol) in toluene (200 ml) were added tri-n-butyltinhydride (9.4 ml, 34.1 mmol) and 2,2'-azo-bis-isobutyronitrile (4.32 g, 26.3 mmol), and the reaction mixture was stirred at 110° C. for 1 hour. After the mixture was cooled down, the solvent was removed. The resulting residue was purified by silica gel column chromatography (hexane/ethyl acetate=3/1) to give the compound 9 (9.21 g, 82%) as a white foam.

UV (MeOH) $\lambda_{max}$ 272.50 nm; $[\alpha]^{20}_D$ −10.00 (c 0.20, MeOH); HR-MS (ESI): m/z calcd for $C_{41}H_{51}N_4O_2Si$ [M+H]$^+$: 659.3781; Found: 659.3757; $^1$H NMR (400 MHz, CDCl$_3$) δ 8.41 (s, 1 H), 7.69 (m, 4 H), 7.41 (m, 6 H), 7.29 (m, 2 H), 7.23 (m, 2 H), 6.92 (d, J=3.6 Hz, 1 H), 6.31 (d, J=3.6 Hz, 1 H), 5.90 (dd, J=7.2, 14.8 Hz, 1 H), 5.38 (m, 1 H), 5.15 (br s, 1 H), 4.33 (dd, J=5.2, 8.4 Hz, 1 H), 3.88 (dd, J=6.4, 10.0 Hz, 1 H), 3.68 (dd, J=7.2, 10.4 Hz, 1 H), 3.05 (m, 1 H), 2.96 (dd, J=7.6, 15.6 Hz, 1 H), 2.76 (m, 1 H), 2.45 (d, J=5.2 Hz, 1 H), 2.29 (m, 2 H), 2.06 (m, 1 H), 1.95 (m, 2 H), 1.55 (s, 1 H), 1.13 (s, 9H), 1.06 (s, 9 H); $^{13}$C NMR (100 MHz, CDCl$_3$) δ 156.3, 151.9, 144.1, 143.9, 135.9, 135.8, 134.3, 129.8, 128.2, 127.8, 127.0, 125.1, 124.6, 121.8, 77.6, 77.2, 76.7, 73.5, 72.2, 63.6, 56.4, 52.8, 46.8, 42.8, 34.9, 34.5, 30.5, 28.6, 27.2, 28.7, 19.4; Anal. Calcd for $C_{41}H_{50}N_4O_2Si$: C, 74.73; H, 7.65; N, 8.30. Found: C, 74.79; H, 7.61; N, 8.25.

Step 7: Preparation of 2-tert-butoxy-4-[4-(indan-1-ylamino)-pyrrolo[2,3-d]pyrimidin-7-yl]-cyclopentanol (Compound 10)

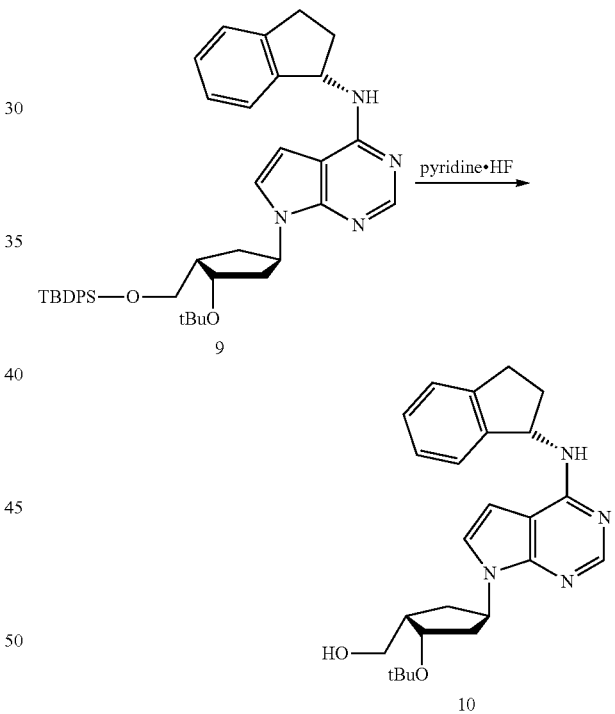

To a solution of the compound 9 (9.21 g, 13.97 mmol) in the mixture of THF and pyridine (1:1, 160 ml) was added dropwise pyridine hydrofluoride (18.42 ml, 190.0 mmol) at 0° C., and the reaction mixture was stirred at room temperature for 1 hour. The mixture was neutralized with saturated aqueous NaHCO$_3$ solution and partitioned between ethyl acetate and water. The organic layer was washed with brine, dried with anhydrous MgSO$_4$, filtered, and evaporated. Then, the residue was purified by silica gel column chromatography (hexane/ethyl acetate=1/3) to give the compound 10 (5.63 g, 99%) as a white foam.

UV (MeOH) $\lambda_{max}$ 273.00 nm; $[\alpha]^{20}_D$ −6.36 (c 1.10, MeOH); HR-MS (ESI): m/z calcd for $C_{25}H_{33}N_4O_2$ [M+H]$^+$:

421.2604; Found: 421.2599; ¹H NMR (400 MHz, CDCl₃) δ 8.34 (s, 1 H), 7.30 (d, J=7.6 Hz, 1 H), 7.22 (d, J=7.2 Hz, 2 H), 7.15 (t, J=6.8 Hz, 1H), 6.88 (d, J=3.2 Hz, 1 H), 6.23 (d, J=3.6 Hz, 1 H), 5.83 (dd, J=7.2, 15.2 Hz, 1 H), 5.28 (m, 1 H), 5.06 (m, 1 H), 4.47 (dd, J=5.6, 10.4 Hz, 1 H), 3.78 (m, 1 H), 3.70 (m, 1H), 3.24 (t, J=5.2 Hz, 1 H), 2.98 (m, 1 H), 2.87 (m, 1 H), 2.68 (m, 1 H), 2.46 (m, 1 H), 2.37 (m, 2 H), 1.93 (m, 2 H), 1.18 (s, 9 H); ¹³C NMR (100 MHz, CDCl₃) δ 156.2, 151.8, 147.9, 143.9, 143.9, 128.3, 126.9, 125.1, 124.5, 121.9, 97.7, 77.6, 77.2, 76.9, 75.5, 74.9, 63.4, 56.4, 53.8, 44.2, 42.2, 34.9, 33.2, 30.5, 28.6; Anal. Calcd for $C_{25}H_{32}N_4O_2$: C, 71.40; H, 7.67; N, 13.32. Found: C, 71.46; H, 7.60; N, 13.35.

Step 8: Preparation of sulfamic acid 2-tert-butoxy-4-[4-(indan-1-ylamino)-pyrrolo[2,3-d]pyrimidin-7-yl]-cyclopentylmethyl ester (Compound 11)

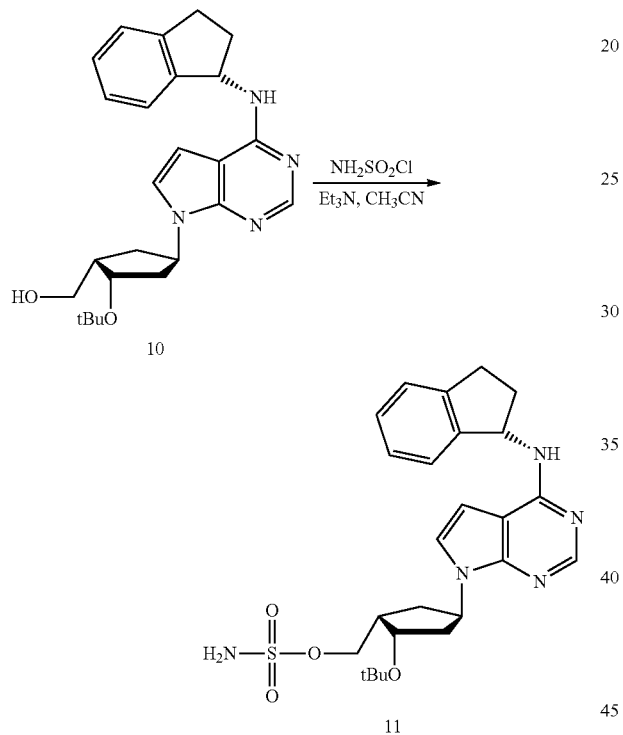

Preparation of 2.0 M solution of chlorosulfonamide in acetonitrile: Formic acid (14.15 ml, 166.0 mmol) was added dropwise to chlorosulfonyl isocyanate (32.0 ml, 162.5 mmol) under nitrogen atmosphere at 0° C. When the addition was completed, the mixture was solidified. To the mixture was added acetonitrile (61.3 ml), and the resulting solution was left to stand under nitrogen source at room temperature overnight.

To a solution of the compound 10 (5.63 g, 13.83 mmol) and triethyl amine (9.7 ml, 0.74 mmol) in acetonitrile (278 ml) was added 2.0 M solution of chlorosulfonamide in acetonitrile (13.83 ml, 27.76 mmol) at 0° C., and the reaction mixture was stirred at room temperature for 45 minutes. Additional 2.0 M chlorosulfonamide solution in acetonitrile (13.83 ml, 27.76 mmol) was added and the mixture was stirred at room temperature for 15 minutes. The reaction was quenched with methanol, and the solvent was removed. The residue was purified by silica gel column chromatography (methylene chloride/methanol=20/1) to give the compound 11 (6.37 g, 92%) as a white foam.

UV (MeOH) λ$_{max}$ 273.00 nm; [α]²⁰$_D$ −18.00 (c 0.50, MeOH); HR-MS (ESI): m/z calcd for $C_{25}H_{34}N_5O_4S$ [M+H]⁺: 500.2332; Found: 500.2331; ¹H NMR (400 MHz, CDCl₃) δ 8.38 (s, 1 H), 7.36 (d, J=7.2 Hz, 1 H), 7.29 (d, J=7.2 Hz, 1 H), 7.22 (m, 2 H), 6.95 (d, J=3.6 Hz, 1 H), 6.31 (d, J=3.2 Hz, 1 H), 5.89 (d, J=6.4 Hz, 1 H), 5.10 (s, 2 H), 4.41 (m, 2 H), 4.26 (m, 1 H), 3.05 (m, 1 H), 2.94 (m, 1 H), 2.76 (m, 2 H), 2.27 (m, 3 H), 2.06 (m, 1 H), 1.97 (m, 1 H), 1.76 (br s, 1 H); ¹³C NMR (100 MHz, CDCl₃) δ 156.4, 151.9, 149.9, 143.9, 143.8, 128.3, 126.9, 125.1, 124.5, 121.9, 121.9, 103.5, 97.9, 77.4, 77.2, 76.9, 74.3, 71.9, 71.3, 56.4, 53.1, 49.0, 42.3, 34.9, 34.3, 30.5, 28.6; Anal. Calcd for $C_{25}H_{33}N_5O_4S$: C, 60.10; H, 6.66; N, 14.02; S, 6.42. Found: C, 60.15; H, 6.71; N, 13.98; S, 6.39.

Step 9: Preparation of sulfamic acid 2-hydroxy-4-[4-(indan-1-ylamino)-pyrrolo[2,3-d]pyrimidin-7-yl]-cyclopentylmethyl ester (Compound 1)

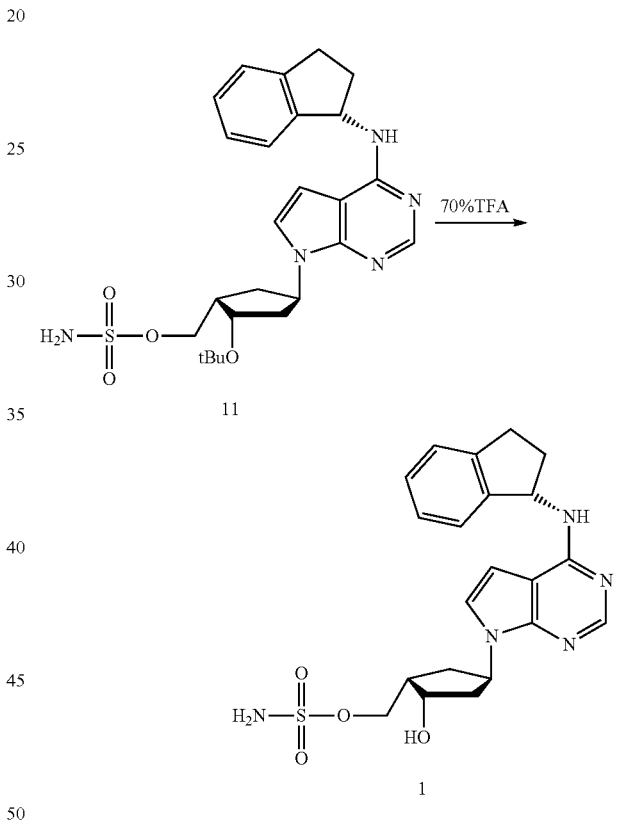

A solution of the compound 11 (6.37 g, 12.72 mmol) in 70% trifluoroacetic acid (149.24 ml) was stirred at room temperature for 2 hours. The solvent was removed and the residue was purified by silica gel column chromatography (hexane/ethylene acetate=1/2) to give the compound 1 (5.08 g, 90%) as a white foam.

UV (MeOH) λ$_{max}$ 279.50 nm; [α]²⁰$_D$ −6.41 (c 2.34, MeOH); HR-MS (ESI): m/z calcd for $C_{21}H_{26}N_5O_4S$ [M+H]⁺: 444.1705; Found: 444.1706; ¹H NMR (400 MHz, CD₃OD) δ 8.17 (d, J=1.6 Hz, 1 H), 7.25 (m, 2 H), 7.18 (m, 2 H), 6.64 (d, J=3.6 Hz, 1H), 5.86 (t, J=7.6 Hz, 1 H), 5.46 (m, 1 H), 4.49 (d, J=2.8 Hz, 1 H), 3.07 (m, 1 H), 2.92 (m, 1 H), 2.80 (m, 1 H), 2.64 (m, 1 H), 2.35 (m, 1 H), 2.25 (m, 2 H), 2.03 (m, 2 H); ¹³C NMR (100 MHz, CD₃OD) δ 152.1, 145.3, 144.6, 128.8, 127.6, 125.7, 125.2, 122.6, 100.5, 73.1, 70.9, 56.9, 54.0, 44.8, 43.6, 34.9, 34.6, 31.1; Anal. Calcd for $C_{21}H_{25}N_5O_4S$: C, 56.87; H, 5.68; N, 15.79; S, 7.23. Found: C, 56.91; H, 5.73; N, 15.82; S, 7.26.

The invention claimed is:

1. A method for preparation of a compound represented by the following formula 1, which method comprises the following steps:

preparing a compound represented by the following formula 5 by hydrogenating a compound represented by the following formula 6 in the presence of a palladium catalyst (step 1);

preparing a compound represented by the following formula 7 by reacting the compound of formula 5 with $NaBH_4$ and $CeCl_3 \cdot 7H_2O$ (step 2);

preparing a compound represented by the following formula 4 by reacting the compound of formula 7 with trimethyl aluminum (step 3);

preparing a compound represented by the following formula 3 by reacting the compound of formula 4 with thionyl chloride to prepare a cyclic sulfite compound, which is then oxidized by means of $RuCl_3$ and $NaIO_4$ (step 4);

preparing a compound represented by the following formula 8 by reacting the compound of formula 3 with $N^6$-indanyl-7-deazaadenine followed by subjecting to hydrolysis (step 5);

preparing a compound represented by the following formula 9 by reacting the compound of formula 8 with phenyl chlorothionoformate to prepare a thiocarbonate compound, which is then reacted with n-$Bu_3SnH$ in the presence of AIBN (step 6);

preparing a compound represented by the following formula 10 by reacting the compound of formula 9. HF (step 7);

preparing a compound represented by the following formula 11 by reacting the compound of formula 10 with chlorosulfonamide (step 8); and preparing a compound represented by the following formula 1 by reacting the compound of formula 11 with TFA (step 9):

[Formula 1]

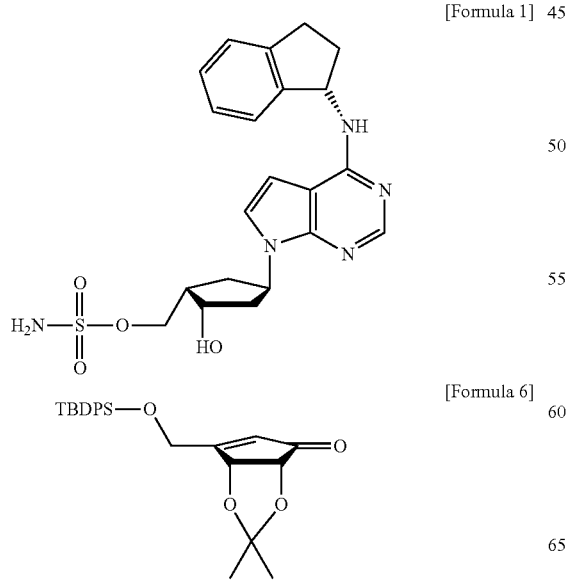

[Formula 6]

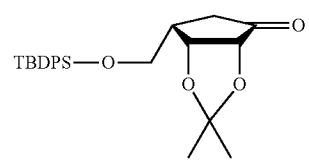

-continued

[Formula 5]

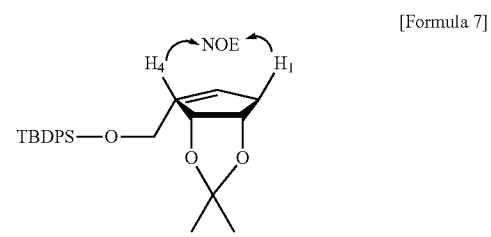

[Formula 7]

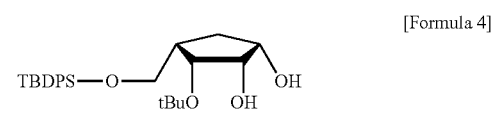

[Formula 4]

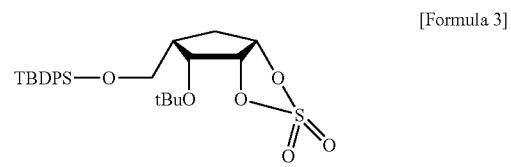

[Formula 3]

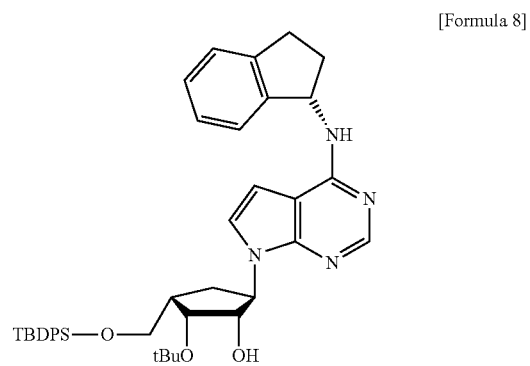

[Formula 8]

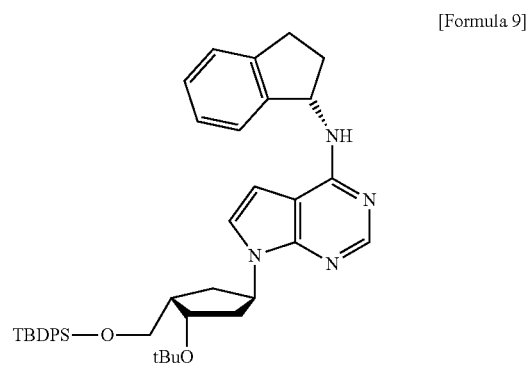

[Formula 9]

-continued

[Formula 10]

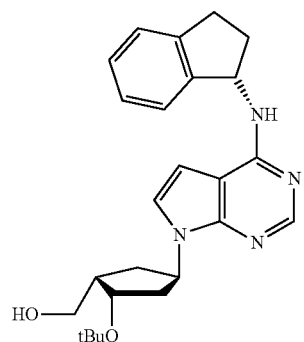

[Formula 11]

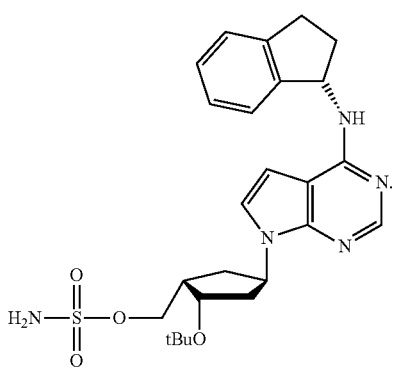

2. The method for preparation of the compound 1 as defined in claim 1, wherein in said step 1) Pd/C is used as palladium catalyst.

3. The method for preparation of the compound 1 as defined in claim 1, wherein in said step 2) the molar ratio of the compound of formula 5 and NaBH$_4$ is in the range of 1:1 to 1:3.

4. The method for preparation of the compound 1 as defined in claim 1, wherein in said step 2) the molar ratio of the compound of formula 5 and CeCl$_3$·7H$_2$O is in the range of 1:1 to 1:3.

5. The method for preparation of the compound 1 as defined in claim 1, wherein in said step 3) the molar ratio of the compound of formula 7 and trimethyl aluminum is in the range of 1:2 to 1:6.

6. The method for preparation of the compound 1 as defined in claim 1, wherein in said step 4) the molar ratio of the compound of formula 4 and thinoyl chloride is in the range of 1:1 to 1:3.

7. The method for preparation of the compound 1 as defined in claim 1, wherein in said step 4) the molar ratio of the cyclic sulfite compound and RuCl$_3$ is in the range of 1:0.2 to 1:1.

8. The method for preparation of the compound 1 as defined in claim 1, wherein in said step 4) the molar ratio of the cyclic sulfite compound and NaIO$_4$ is in the range of 1:1 to 1:3.

9. The method for preparation of the compound 1 as defined in claim 1, wherein in said step 5) the molar ratio of the compound of formula 3 and $N^6$-indanyl-7-deazaadenine is in the range of 1:1 to 1:3.

10. The method for preparation of the compound 1 as defined in claim 1, wherein in said step 5) the hydrolysis is carried out by means of hydrochloric acid, sulfuric acid or nitric acid.

11. The method for preparation of the compound 1 as defined in claim 1, wherein in said step 6) the molar ratio of the compound of formula 8 and phenyl chlorothionoformate is in the range of 1:1 to 1:5.

12. The method for preparation of the compound 1 as defined in claim 1, wherein in said step 6) the molar ratio of the thiocarbonate compound and AIBN is in the range of 1:1 to 1:3.

13. The method for preparation of the compound 1 as defined in claim 1, wherein in said step 6) the molar ratio of the thiocarbonate compound and n-Bu$_3$SnH is in the range of 1:1 to 1:4.

14. The method for preparation of the compound 1 as defined in claim 1, wherein in said step 7) the molar ratio of the compound of formula 9 and pyridine.HF is in the range of 1:1 to 1:10.

15. The method for preparation of the compound 1 as defined in claim 1, wherein in said step 8) the molar ratio of the compound of formula 10 and chlorosulfonamide is in the range of 1:2 to 1:5.

16. The method for preparation of the compound 1 as defined in claim 1, wherein in said step 9) the molar ratio of the compound of formula 11 and TFA is in the range of 1:10 to 1:100.

* * * * *

UNITED STATES PATENT AND TRADEMARK OFFICE
CERTIFICATE OF CORRECTION

PATENT NO. : 8,716,304 B2
APPLICATION NO. : 13/425212
DATED : May 6, 2014
INVENTOR(S) : Lak Shin Jeong et al.

It is certified that error appears in the above-identified patent and that said Letters Patent is hereby corrected as shown below:

Title Page, Item (30):
--June 22, 2011 (KR).....................10-2011-0060898-- was omitted from the face of the patent.

In the Claims

Column 21, Line 35:
"formula 10 by reacting the compound formula 9. HF" should read, --formula 10 by reacting the compound of formula 9 with pyridine·HF--.

Column 23, Line 40:
"the compound of formula 5 and $CeCl_3$. $7H_2O$ is in the range" should read, --the compound of formula 5 and $CeCl_3·7H_2O$ is in the range--.

Column 24, Line 35:
"the compound of formula 9 and pyridine.HF is in the range of" should read, --the compound of formula 9 and pyridine·HF is in the range of--.

Signed and Sealed this
Seventeenth Day of March, 2015

Michelle K. Lee
*Director of the United States Patent and Trademark Office*